(12) United States Patent
Lehmann

(10) Patent No.: US 6,710,028 B2
(45) Date of Patent: *Mar. 23, 2004

(54) METHOD FOR TREATING DISTURBANCES IN IRON METABOLISM USING A COMBINATION OF ERYTHROPOIETIN AND IRON

(75) Inventor: Paul Lehmann, Worms (DE)

(73) Assignee: Roche Diagnostics GmbH, Mannheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 10/047,749

(22) Filed: Oct. 23, 2001

(65) Prior Publication Data
US 2002/0094948 A1 Jul. 18, 2002

Related U.S. Application Data

(62) Division of application No. 09/381,248, filed on Sep. 14, 1999.

(30) Foreign Application Priority Data

Mar. 18, 1997 (EP) .................................. PCT/EP97/01343

(51) Int. Cl.⁷ .............................................. A01N 37/18
(52) U.S. Cl. ......................................................... 514/2
(58) Field of Search ................... 514/8, 21, 2; 530/380, 530/397

(56) References Cited

U.S. PATENT DOCUMENTS

| | | | |
|---|---|---|---|
| 4,745,099 A | | 5/1988 | Akamatsu et al. |
| 5,376,632 A | * | 12/1994 | Konings et al. ................ 514/8 |
| 5,541,158 A | * | 7/1996 | Vance et al. .................... 514/8 |
| 6,333,306 B1 | * | 12/2001 | Lehmann ......................... 514/8 |
| 6,372,715 B1 | * | 4/2002 | Kaltwasser et al. ............. 514/2 |
| 2002/0160956 A1 | * | 10/2002 | Lehmann et al. .............. 514/12 |

FOREIGN PATENT DOCUMENTS

| | | | | |
|---|---|---|---|---|
| EP | 0 205 564 | | 12/1986 | |
| EP | 0 286 439 | | 10/1988 | |
| EP | 0 411 678 | | 2/1991 | |
| EP | 0 286 439 A1 | * | 10/1998 | .......... A61K/37/24 |
| WO | WO 97/09996 | * | 3/1997 | .......... A61K/38/18 |

OTHER PUBLICATIONS

Pincus et al. (Aug. 1990) "Multicultural Study of Recombinant Human Erythropoletin in Correction of Anemia in Rheumatoid Arthritis." The American Journal of Medicine 89(2): 161–168.*

MacDougall (1994) Monitoring of iron status and iron supplementation in patients treated with erythropoietin. Current Opinion in Nephrology and Hypertension 3(6): 620–625.*

Taylor et al. (1996) Regular low–dose intravenous iron therapy improves response to erythropoietin in haemodialysis patients. Nephrology, Dialysis, and Transplantation 11(6): 1079–1083.*

Means, Jr. (1995) Erythropoietin in the treatment of anemia in chronic infectious, imflammatory, and malignant diseases. Current Opinion in Hematology 2(3): 210–213.*

Grutzmacher et al. (1992) Effect of recombinant human erythropoietin on iron balance in maintenance hemodialysis: theorectical considerations, clinical experience, and consequences. Clinical Nephrology 38 Supplement 1: S92–S97.*

Adamson (1996) Erythropoietin, Iron Metabolism, and Red Blood Cell Production. Seminars in Hematology 33(2): 5–9.*

Mercuriali and Inghilleri (1995) Iron Administration to optimise the effect of r–HuEPO in the surgical setting. Erythopoiesis: New Dimensions in the Treatment of Anemia 6(3):67–76.*

Grützmacher P., et al., Clinical Nephrology, vol. 38, pp. 92–97, 1992.

Sunder–Plassmann G., et al., Journal of the American Society of Nephrology, 5, (3), pp. 478 (1994).

Gasche C., et al., Dig. Dis. Sci., 39, (9) pp . 1930–4 (1994).

Sunder–Plassmann G., et al., Nephrology Dialysis Transplantation, 10, (11), pp. 2070–2076 (1995).

Mercuriali F. et al., Erythropoiesis: New Dimensions in the Treatment of Anaemia, 6/3, pp. 67–76, (1995).

Sunder–Plassmann G., et al., Nephrology Dialysis Transplantation , 11, (6), pp. 1797–1802, (1996).

Taylor J. E., et al., Nephrology Dialysis Transplantation, 11, (6), pp. 1079–1083, (1996).

* cited by examiner

Primary Examiner—Elizabeth Kemmerer
Assistant Examiner—Christopher James Nichols
(74) Attorney, Agent, or Firm—George W. Johnston; Patricia S. Rocha-Tramaloni

(57) ABSTRACT

A pharmaceutical composition comprising 250–20,000 U of an EPO preparation and 5–20 mg of a Fe(III) complex is disclosed. This pharmaceutical composition is useful in treating anaemias as well or as haemodialysis patients.

13 Claims, No Drawings

METHOD FOR TREATING DISTURBANCES IN IRON METABOLISM USING A COMBINATION OF ERYTHROPOIETIN AND IRON

This is a divisional of copending application Ser. No. 09/381,248, filed Sep. 14, 1999.

The present invention concerns pharmaceutical combination preparations containing erythropoietin and iron preparations. The preparations are used particularly to optimize erythropoiesis for the treatment of diseases in which it is intended to stimulate the formation of erythrocytes.

The subject matter of the present invention is a pharmaceutical combination preparation comprising 250–20,000 U of an erythropoietin preparation and 1–40 mg of an equivalent amount of iron ions of a physiologically compatible iron preparation in which the erythropoietin preparation and the iron preparation can be present in separate forms of administration or in a uniform administrative form.

It is known that anaemia and in particular the anaemia of haemodialysis patients caused by transfusion can be treated with recombinant erythropoietin (rhEPO). Anaemia in chronic diseases is worldwide the second most frequent form of anaemia.

A reduced new production of erythrocytes is in the foreground of anaemias that are caused by reduced erythropoiesis in the bone marrow or by disturbances of iron re-utilization. When the new formation of erythrocytes declines daily by 1%, anaemia cannot be clinically diagnosed until after 1–3 weeks. The daily iron requirement for a normal erythropoiesis is 25 mg. Of this only about 1 mg is derived from the food, the main requirement is normally met by re-utilization of the haemoglobin iron after the degradation of aged erythrocytes. The release of iron from the reticular cells is greatly reduced in chronic diseases. The iron is retained in the reticuloendothelial system and is no longer available for erythropoiesis. One therefore also speaks of an "inner iron deficiency" in which normal compensation mechanisms are incompletely triggered. A reticulocytopenia and an absence of a hyperplasia of the erythropoiesis that would be needed to compensate for the anaemia are typical. A reduced erythropoietin secretion or activity may also be an additional pathogenetic factor. A significant change in iron metabolism is for example the absence of a compensatory increase in transferrin formation. The underlying disorder is therefore the lack of iron release from the iron stores (in the reticuloendothelial cells) into the plasma (and thus also into the erythron) as a result of which the normal compensation mechanisms are not triggered. The administration of recombinant erythropoietin is utilized therapeutically to significantly increase the number of erythrocytes.

In clinical chemistry the concentration of serum ferritin is determined to diagnose anaemia and disorders of iron metabolism. If a real iron deficiency occurs in addition to the anaemia of chronic diseases then there is no increase in ferritin (it usually remains below 90–95 ng/ml). If at the same time there are clinical signs of infection, inflammation or malignant disease, this value indicates a combination of iron deficiency and anaemia accompanied by a chronic disease. Since in these diseases the serum ferritin can also react in the sense of an acute phase protein, the erythrocyte ferritin can be utilized better diagnostically.

The total body iron is ca. 3.5 g in men and 2.5 g in women. Iron is actively metabolised and present in storage compartments. In the active pool of a man an average of 2100 mg is present in haemoglobin, 200 mg in myoglobin, 150 mg in enzymes of the tissue (haem and non-haem) and 3 mg in the iron transport compartment. Iron is stored intracellularly in the tissue as ferritin (700 mg) and as haemosiderin (300 mg).

The bioavailability of the iron can be pathophysiologically disturbed resulting in a reduced iron absorption in the body. Of the approximately 10 mg that is daily available through the diet an adult only absorbs about 1 mg. In iron deficiency the absorption increases, but seldom above 5–6 mg, if no additional iron is supplied. The exact mechanism for the absorption of iron has not been elucidated. The mucosal cells of the small intestine play a decisive role in the regulation. The most important signal for the mucosa appears to be the total iron content of the body. It has been shown that the serum ferritin concentration correlates inversely with the amount of absorbed iron.

The iron is transferred from the intestinal mucosal cells to transferrin. This iron transport protein has two iron binding sites. It is synthesized in the liver. Hence there is a mechanism whereby iron is received by cells (e.g. mucosa of the small intestine, macrophages) and transferred to specific membrane receptors of erythrocytes, placental cells or liver cells. The transferrin-iron-receptor complex reaches the inside of the erythrocyte precursor cells by endocytosis where the iron is passed onto the mitochondria. Here haem is formed from iron and protoporphyrin.

Iron that is not required for erythropoiesis is transferred by transferrin into two types of storage pool. Ferritin is the most important store. This is a heterogeneous family of proteins which surround an iron core. It is soluble and represents the active storage form in the liver (hepatocytes), bone marrow, spleen (macrophages), erythrocytes and in the serum ( about 100 ng/ml). The tissue ferritin pool is very labile and is rapidly available when iron is required. Circulating serum ferritin is derived from the reticuloendothelial system and its circulating concentration parallels that of the total body iron (each ng/ml corresponds to 8 mg iron store).

In the case of haemodialysis patients it has turned out that the iron requirement of patients treated with rhEPO is quite considerable. As a rule an additional iron therapy is usually carried out on these patients since EPO can only develop an optimal action when the corresponding iron stores in the body are as full as possible. Hitherto high doses of iron preparations have been commonly administered to fill up the iron stores as much as possible. However, excessive doses of iron preparations can also lead to undesired side-effects in the patients. In particular the intravenous administration of iron preparations is not physiologically safe due to the extreme toxicity of iron ions. The use of certain iron preparations is usually warned against for patients with known allergic reactions e.g. for asthmatics. It is possible to assess the fill status of the iron stores by determining the protein ferritin and by determining the transferrin saturation (M. Wick, W. Pingerra, P. Lehmann "Eisen-stoffwechsel, Diagnose und Therapie der Anämien", pages 5–14, 38–55, 65–80, 94–98; third extended edition, September 1996, Springer publishers Wien, N.Y.) whereby the transferrin saturation represents the flow of iron from the depots to the bone marrow whereas the serum ferritin value is a measure for stored iron.

The iron stores are considered to be "full" when the serum ferritin is <150 µg/l and a transferrin saturation of 20% is present. P. Grützmacher et al. describe in Clinical Nephrology, Vol. 38, No. 1, 1992, p. 92–97 that under these conditions one can assume a maximum response to EPO therapy.

In the iron therapy of EPO-treated dialysis patients one currently refers to a "correction phase" and a "maintenance phase". In the correction phase the highest possible doses of iron preparations are administered in order to fill up the iron stores as rapidly as possible. In this case suitable iron preparations are expediently administered as an intravenous bolus injection. In the maintenance phase the iron stores are then kept filled with low doses of iron. Suitable iron preparations are no longer administered in this phase as a rapid bolus injection but in the form of conventional infusion preparations or by oral administration.

The iron requirement of a haemodialysis patient treated with rhEPO can be quite considerable in the correction as well as in the maintenance phase. 150 mg iron is required to synthesize 1 g/dl haemoglobin in the correction phase that either has to be covered by endogenous iron stores or has to be supplied exogenously. The iron requirement is also increased in the maintenance phase since small losses of blood occur in haemodialysis patients with every treatment. The iron loss is estimated to be about 1000 mg iron (3 mg/day) over a period of one year. In the long term such a loss can only be compensated exogenously. In principle oral and intravenous forms of administration are available for this.

Since the oral iron absorption is only about 1 mg/day and under extreme loading (with an oral administration of about 300 mg Fe (III)/day) is less than 3 mg/day, an intravenous administration of relatively large amounts of iron is increasingly preferred. On the German pharmaceutical market two iron preparations are at present available that can be administered intravenously. These are the drugs "Ferriecit" and "Ferrum Vitis". Ferriecit is an iron (3) gluconate complex whereas Ferrum Vitis is an iron (3) hydroxide saccharate complex.

The diverse problems of a high-dose, long-term oral iron therapy can be relatively simply circumvented by the intravenous subcutaneous administration of physiologically compatible iron(III) salts during the haemodialysis treatment since in this case there is a safe intravenous subcutaneous access and the injection can be carried out without further stress to the patient. In recent years this procedure has become more and more wide-spread since one assumed that the preparations "Ferrlecit" and "Ferrum Vitis" are forms of administration that are relatively free of side effects. However, side effects in connection with the Ferrlecit therapy in autologous blood transfusion have now been reported and the indication for parenteral Ferrlecit therapy has been considerably restricted. Attention has been called to the possibility of circulatory reactions including even collapse as well as to the possible occurrence of anaphylactic reactions. Furthermore the maximum permissible daily dose has been prescribed as two ampoules of 5 ml corresponding to 125 mg iron.

Hence the intravenous administration of both iron preparations is not trivial since side effects may occur when the two drugs are administered, particularly when relatively large amounts have to be injected relatively rapidly. Moreover the intravenous administration of the iron preparations can cause problems even including acute phase reactions if the iron dose is too high or the dose is not optimally matched with the EPO dose.

Obviously the high iron dosages that have to be administered to EPO-treated dialysis patients are disadvantageous. The risk of a myocaridal infarction increases and there is also a significant increase in the risk of developing an iron cirrhosis. Within the framework of treating dialysis patients an adequate supply of iron as well as a suitable method for determining the concentration of iron in body fluids to identify a possible iron deficiency is of considerable therapeutic utility since an inadequate iron availability is one of the main causes of an inadequate action of EPO or of an EPO resistance.

An excessive dosage of preparations containing iron can also lead to iron poisoning. Elemental iron has a toxic effect on the gastrointestinal tract, the cardiovascular and the central nervous system. The oral lethal dose of elemental iron varies between 200 and mg/kg. The most frequently used iron tablets are ferrosulfate (contains about 20% elemental iron), ferrofumarate (contains about 30% elemental iron) or ferrogluconate (contains about 10% elemental iron).

There are four typical stages of iron poisoning: stage I (within the first 6 hours after poisoning): vomiting, diarrhoea, hyperirritability, abdominal pain, fits, apathy and coma can occur. Irritations of the gastrointestinal mucosa can lead to a haemorrhagic gastritis. When there are high serum iron levels tachypnoea, tachycardia, hypotension, shock, coma and metabolic acidosis can occur. Stage II (within the first 10–14 hours after poisoning): During a latency period which can last up to 24 hours an apparent improvement occurs. Stage III (12–48 hours after poisoning): shock, hypoperfusion and hypoglycaemia occur. The level of serum iron can be normal. Liver damage with increased GPT, fever, leucocytosis, coagulation disorders, T-inversion in the ECG, disturbances of orientation, restlessness, apathy, tendency to fits, coma, shock, acidosis and death can occur. Stage IV (2–5 weeks later): possible complications by a pylorus, antrum or another intestinal obstruction, a liver cirrhosis or damage of the central nervous system may be in the foreground.

The object of the invention was to provide a combination preparation of an erythropoietin preparation and an iron preparation which contains an optimally balanced amount of EPO and iron ions for the treatment of disturbances of iron metabolism. In particular it should be possible to avoid the above-mentioned risks, especially the acute phase reactions with the aid of these combination preparations. Furthermore an optimal EPO action as well as the avoidance of an EPO resistance should be achievable in patients that are treated with rhEPO.

The combination preparation according to the invention comprises 250–20,000 U of an erythropoietin preparation and 1–40 mg of an equivalent amount of iron ions of a physiologically compatible iron preparation in particular of a Fe(II) or Fe (III) complex in which the EPO preparation and the iron preparation are present as combination preparations. Within the sense of the present invention such EPO preparations are for example used having a content of less than 2,000 U or a content of more than 7,000 U of the EPO preparation.

Within the sense of the present invention the term "combination preparations" should not only be understood as those packs of pharmaceutical products in which the EPO preparation and the iron preparation are. present manufactured side by side in a saleable packaging unit (so-called combination pack) but also those packs of pharmaceutical products which either contain a suitable amount of an EPO preparation or a suitable amount of an iron preparation in the form of an individual preparation in which the individual preparations are formulated, with regard to the amount of constituents, in such a manner that they can be administered within the sense of the invention together with the other respective preparation for a combined administration. In these cases the pharmaceutical manufacturers or the drug importers usually enclose with the preparations a package insert for drugs that is legally required in many countries which contains instructions or information about the combined administration of the individual preparations. The combination preparations may be preferably in the form of a uniform form of administration in which the respective amount of EPO and iron preparation are present side by side in a container.

Within the sense of the invention oral or parenteral forms of administration come into consideration as iron preparations. These can in principle be individual preparations which contain a physiologically compatible iron salt or an iron complex compound as the active substance or they can also be combination preparations which, in addition to the physiologically compatible iron preparation, contain further active substances such as e.g. vitamins, folic acid, thiamine chloride, riboflavin, pyridoxine, ascorbic acid, nicotinamide, and calcium pantothenate.

Physiologically compatible iron salts or iron complex compounds are for example iron(II) sulfate, iron(II) fumarate, iron(III) citrate, iron(II) gluconate, iron(II) succinate, iron(II) chloride, iron(II) glycine-sulfate complex, iron(II) aspartate, sodium-iron(III) gluconate complex, iron(III)-hydroxide-polymaltose complex or ferri-sorbitol citrate complex. Preferred iron preparations are in particular Fe(III) complexes especially those with a molecular weight between 30,000 and 100,000 D. Fe(III) saccharate is particularly preferred. In this case the commercially available preparation "Ferrum Vitis" (Neopharma Co. Germany) can be used. The low iron dosage according to the invention also enables labile iron complexes such as iron gluconate (MW ca. 1000 D; Ferrlecit) to be used in the combination preparation although these labile iron complexes release relatively large amounts of ionized iron which would lead to toxicities if large amounts were to be administered intravenously.

In the following when reference is made to the amount of the iron preparation this is always understood as the equivalent amount of iron ions, Fe(II) or Fe(III) ions, to be administered. This standardization enables calculation of the amount of any desired iron preparation on the basis of its known molecular weight. In the case of iron(III) gluconate×2 $H_2O$ the amount of iron is for example 80.5 mg if an amount of 695 mg of the iron preparation is administered. If for example 280 mg anhydrous iron(II) succinate is administered the amount of iron is 95.2 mg.

Within the sense of the present invention such active substances come into consideration as suitable erythropoietin preparations which are comparable to human EPO with regard to physiological action. Suitable EPO preparations are for example the recombinant human EPO (rhEPO; cf. European Patent document EP 0,205,564 and EP 0,411,678) and also appropriate modifications of such proteins. Those proteins with a higher or lower molecular weight than 34,000 Da (molecular weight of the urinary EPO) come into consideration as modifications and also isoforms of the enzyme or proteins with different glycosylation. In particular it is also possible to use proteins which are chemically modified by PEG (polyethylene glycol). Furthermore it is basically also possible to use those proteins which are derived from the amino acid sequence of natural EPO with a length of 166 amino acids by deletions, substitutions or extensions of single or several amino acids. Such proteins have essentially comparable physiological properties to rhEPO. In particular such proteins have biological properties that induce bone marrow cells to increase the production of reticulocytes and red blood cells and/or to increase the synthesis of haemoglobin or iron uptake. Instead of such proteins it is also possible to use low molecular substances that are referred to as EPO mimetics and which bind to the same biological receptor. These mimetics can also preferably be administered orally. The amount of such proteins or mimetics that should be administered is determined by comparing the biological activities of EPO and of these active substances.

For the treatment of haemodialysis patients the combination preparation according to the invention comprises in particular 250 to 15,000 U (instead of the abbreviation "U" it is also possible to use the abbreviation "IU" for international units) of an EPO preparation, in particular 500 to 10,000 U. Preferred dosages are 250 U, 500 U, 1,000 U, 2,000 U, 5,000 U, 7,500 U and 10,000 U per single dose. The amount of iron ions is preferably up to 30 mg, in particular 3–20 mg, preferably 5–20 mg and especially preferably about 10 mg. For the treatment of anaemia patients the optimal dose is 500 to 10,000 U preferably about 1,000–3,000 U. In this case the amount of iron ions is preferably up to 30 mg, for example 3–15 mg, in particular about 5 mg.

The concentrations of the EPO preparation and the iron complex according to the invention allow, as a combination, an optimal control and treatment of haemodialysis or anaemia patients and, in the case of intravenous iron therapy, do not lead to acute phase reactions.

Treatment with the combination preparation is carried out once to five times, preferably up to four times weekly, the total amount of iron ions per patient not exceeding 100 mg per week. When treating haemodialysis patients a total amount of 80 mg in particular 60 mg iron ions per week should not be exceeded. When treating anaemia a total amount of 40 mg, in particular 20 mg, iron ions per week should preferably not be exceeded. A particular advantage of the combination preparation according to the invention in clinical practice is that it can be used in the correction as well as in the maintenance phase of an iron therapy of haemodialysis patients without causing toxicities. Previously different amounts of iron were administered, lower dosages of iron ions being firstly administered in the correction phase compared to those of the maintenance phase. Surprisingly this different dosage is no longer necessary when using the combination preparations according to the invention. The amount of the erythropoietin preparation and iron preparation are so optimally matched in the combination preparations according to the invention that it is not necessary to differentiate between the maintenance dose and correction dose. This increases the safety in treating the patients since there is no longer a possibility of confusion with regard to the optimal dosage of the iron preparation.

When using the combination preparations it is also possible to administer the EPO preparation and the iron complex in a so-called fixed combination i.e., in a single pharmaceutical formulation which contains both compounds. These can for example be injection solutions, infusion solutions or lyophilisates which are for example filled into ampoules. This form of administration has the advantage that the EPO preparation is stabilized by the iron complex during manufacture and storage of the form of administration. The fixed combination of two active substances in the form of a lyophilisate has the further advantage of a simple and safe handling. The lyophilate is dissolved in the ampoule by adding standard pharmaceutical injection media and administered intravenously.

It is also possible to provide the EPO preparation and iron complex in the form of separate pharmaceutical formulations. As a rule this is achieved in the form of a single packaging unit which comprises two containers the first being a suitable form of administration for the erythropoietin preparation (lyophilisate, injection or infusion solution) and the second container represents a suitable form of administration for the iron preparation. The packaging units can also contain several individual dosage preparations of the erythropoietin preparation or the iron preparation so that one packaging unit for example comprises the required number of individual forms of administration for a certain time period (e.g. for the weekly dosage).

This free combination which can be provided in a single packaging unit (pharmaceutical pack) has the advantage that each patient to be treated can be individually assigned a directly ascribable amount of an EPO preparation and an iron preparation. Such combination preparations have the additional advantage of a more certain therapy success since in each case an optimally matched amount of the individual preparations is fixed and a confusion with other commercially available individual preparations that are provided in various dosages can be largely excluded. Moreover it should be kept in mind that pharmaceutical preparations with different dosages are often on the market in different countries due to national requirements and thus there is an increased risk of mistakes with varying quantity ratios of the individual active substances (EPO preparation and iron complex). Furthermore the combination preparations according to the invention minimize the risk of an inadvertently high iron dose which may occur when conventional iron preparations from separate pharmaceutical packs are used together with an erythropoietin preparation dose. The combination preparations according to the invention ensure a safe therapy and simple handling by the attending staff or in the context of self medication carried out by the patient. In the present case it is also for example possible to provide an active substance as an injection solution and the other active substance (iron complex) as a form of administration for oral administration.

In the case that the EPO preparation is provided as a lyophilisate the pharmaceutical packs (combination packs) contain the appropriate amount of the EPO preparation in glass ampoules or in carpoules. The iron preparation can be present in a solid form (tablet, powder, granulate, lyophilisate, etc.) and also in a liquid form in a separate container. Furthermore the combination pack preferably contains a reconstitution solution in order to either dissolve the active substance lyophilisate alone or also together with the solid iron preparation. If the iron preparation is present as a ready-to-use solution, the solution can be mixed together with the EPO solution if it is intended to jointly administer EPO and the iron preparation. In principle the iron preparation can also be provided as a concentrate for addition to conventional infusion solutions as a result of which it is possible to administer more slowly over several hours. In this case a small volume of the solution containing iron complex (about 0.6–10 ml) is added to the ready-to-use injection solution of about 500–1000 ml.

Combination preparations within the sense of the present invention are also those packaging units that are adjusted to an amount of the EPO preparation and the iron preparation that is optimal for a weekly administration. Weekly doses of 5,000–50,000 U of an EPO preparation are advantageously administered. This total dose can be divided into several partial doses for a daily administration (i.e. 7 times per week) or for the administration of 1–6 portions per week. The amount of the iron preparation to be administered weekly can optionally also be divided into an amount corresponding to the total weekly dose or also into several portions for a multiple administration per week together with the erythropoietin preparation.

A further possibility within the sense of the present invention is to provide individual forms of administration of the erythropoietin preparation and of the iron preparation as independent pharmaceutical preparations, the individual preparations being formulated such that they contain the required amount of the individual substances of the for the combination according to the invention EPO preparation and iron complex. As a rule the pharmaceutical packs contain the prescribed package inserts which include a corresponding note regarding the combined administration with EPO or with iron preparations in the required amount. An appropriate note can also be printed on the pharmaceutical pack (secondary packaging) or on the primary packaging (ampoule, blister strip). Hence in the case of a pharmaceutical preparation containing EPO with 250–20,000 units EPO it is for example noted that this preparation should be in particular administered together with an iron complex preparation containing 1–40 mg iron, preferably 5–30 mg iron. Conversely in the case of iron preparations reference is made to a combined administration together with 250–20000 U of an erythropoietin preparation.

A further possibility of providing EPO preparations is to provide appropriate multi-dose preparations which contain the EPO preparation in larger amounts compared to individual doses. Such preparations are especially suitable for use in hospitals where many patients are treated daily. These multi-dose preparations contain the EPO preparations in doses of up to 500,000 U in particular up to 100,000 U or 50,000 U. The advantage of the multi-dose preparations is that they enable the medical staff to take out any desired dose of the EPO preparation by for example withdrawing appropriate amounts of volume of the injectable, solution. This is in particular advantageous when treating patients with different dose requirements of the active substance or when treating children who require a smaller dose of the EPO preparation. An injection solution, preferably freshly prepared at the start of the day, of for example 100,000 U of an EPO preparation could be used to treat all patients who need treatment during that day without having to prepare separate injection solutions for each individual patient. This can lead to a significant saving of time or reduction of the workload of medical staff. The individual EPO dosages are preferably withdrawn in the range of 250 U, 500 U, 1000 U and 10,000 U.

The multi-dose preparations can also be present in the form of solutions which are filled into carpoules. These carpoules are suitable for use in so-called pens which enable an individual withdrawal of doses and administration by the patient himself. Such carpoules for example contain the EPO preparation in an amount of 10,000 or 20,000 U whereby dose intervals of for example 250 U, 500 U, 1,000 U and 2,000 U are achievable by appropriate setting of the withdrawn volume.

The pharmaceutical forms of administration are manufactured by conventional processes known in galenic technology using standard pharmaceutical auxiliary substances.

When a combination therapy is carried out with the combination preparation according to the invention it is easy to decide the weekly maximum dosage by determining the diagnostic parameters for iron status in particular the parameters iron, transferring transferrin saturation and ferritin. It has turned out that a patient in the correction and maintenance phase is optimally controlled when

| ferritin is: | 100–300 µg/l (corresponds to 800–1200 mg depot iron (III)) and the |
|---|---|
| transferrin saturation is: | 20–40%. |

The ferritin concentration is preferably at least 125 µg/l, in particular at least 150 µg/l and maximally up to 270 µg/l and in particular maximally up to 250 µg/l. The iron concentration is preferably between 10–20 µmol/l (corresponds to about 56–112 µg/dl) and the transferrin concentration is between 30–60 µmol/l (corresponds to about 240–480 mg/dl). The transferrin saturation is defined as the ratio of the serum/plasma iron concentration to the serum/plasma transferrin concentration (multiplied by a correction factor of 1.41). This is a dimensionless number which is independent of the hydration status of the patient. The transferrin saturation is calculated from the formula:

transferrin saturation (%)=(iron[µg/dl]×100)/(transferrin[mg/dl]×1.41)

An optimal control of the patient is achieved when the ratio of the transferrin saturation (in %) to the ferritin concentration (in µg/l) is in the range of 5–40%. This parameter is defined as the transferrin/ferritin saturation (TfF saturation). It is calculated from the formula:

TfF-saturation=(transferrin saturation in %)×100(ferritin[µg/l])

The value for this parameter is preferably in the range of 10–40, in particular of 15–25 [%×1/µg].

This parameter is used to diagnostically check the optimal control of the patient for example when administering 1 to 6 ampoules, preferably up to 3, 4 or 5 ampoules per week (one ampoule contains 500–7,500 U rhEPO and 1–20 mg iron complex).

In order to be certain to exclude undesired side effects, the acute phase parameter CRP (5 mg/l±100%) [CRP=C-reactive protein] is measured, CRP being regarded at present as the best protein marker for an inflammatory reaction. In addition the liver parameters GPT (glutamate-pyruvate transaminase), GOT (glutamate-oxaloacetate transaminase) and γ-GT (gamma glutamyl transferase) can also be determined which should be in the following ranges (determination at 37° C.): GPT: <50 U/l; GOT: <50 U/l; γ-GT: <40 U/l. At present GPT is the primary parameter in liver diagnostics.

Furthermore the haematological control parameters such as the haematocrit (red blood cells as a proportion of the total volume) or the increase of hypochromic erythrocytes may optionally be used. If there are relatively large increases in the control parameters, the weekly iron dose must be reduced and then rhEPO should be additionally administered. If the values for the control parameters, above all the transferrin saturation, are low then the weekly iron dose must be increased.

Furthermore it was surprisingly found within the sense of the present invention that an individual therapeutic dose of EPO and of iron ions that is optimal for the patient for the treatment of anaemia can be determined by determining the soluble TfR (transferrin receptor). The optimal therapeutic dose of EPO and of iron(III) is achieved when the concentration of the soluble TfR no longer increases. In order to ensure that sufficient mobilizable iron is present, the i.v. iron dose and the EPO dose are alternately increased until a plateau is reached. This corresponds to a concentration of 1,500–2,000 µg/l TfR.

When carrying out the combination therapy using the combination preparation according to the invention for the treatment of anaemia it is very simple to decide the weekly maximum dosage by determining the diagnostic parameters transferrin receptor (TfR), ferritin and the ratio of TfR to ferritin. It turned out that the patient is optimally controlled in the correction and maintenance phase when

| ferritin is: | 100–300 µg/l (corresponds to 400–1200 mg depot iron (III)) |
|---|---|
| TfR/ferritin is: | >15. |

The TfR concentration is advantageously between 1500–2500 µg/l. The ratio of the concentration of TfR (in µg/l) to ferritin (in µg/l) is in particular in the range of 15–35, preferably having values above 20.

The optimal control of the patient is diagnostically checked using these parameters for example when administering 1 to 6 ampoules preferably up to 3, 4 or 5 ampoules per week (one ampoule contains for example 3000 U rhEPO and 5 mg iron complex). In this case these are in particular not haemodialysis patients but rather those patients that are under treatment with EPO and/or iron preparations for an anaemia of a different genesis.

In order to be certain to exclude undesired side effects, the acute phase parameter CRP (2–10 mg/l) [CRP=C-reactive protein] is measured. In addition the liver parameter GPT (glutamate-pyruvate transaminase) can be determined which should be <50 U/l at 37° C. (<30 Ug/l at 25° C). Furthermore the haematological control parameters such as the haematocrit (red blood cells as a proportion of the total volume) or the increase of hypochromic erythrocytes may optionally be used. In this case the reticulocytes can increase to a value of up to 15/1000–30/1000. The typical haemoglobin concentration is 12–18 g/dl. If there is a larger increase in the soluble TfR value, the weekly iron dose must be increased up to 35 mg. If there is a decrease in the soluble TfR values, the weekly EPO dose must be increased.

The iron status is determined by analysing samples of body fluids (blood, serum, urine etc.) from the respective patients. In particular the concentration of iron, transferrin, ferritin, transferrin receptor, the transferrin saturation and the transferrin/ferritin saturation are determined to determine the iron status. In the case of haemodialysis patients the parameters iron, transferrin, ferritin and transferrin saturation are preferably determined by conventional analytical methods. The determination of the transferrin/ferritin saturation value is of particular relevance. In the case of anaemia patients whose anaemia is not caused by haemodialysis, the ferritin concentration and the concentration of the transferrin receptor are determined in particular. The determination of the ratio of transferrin receptor to ferritin (transferrin receptor/ferritin saturation value) is especially relevant.

In this sense an optimal combination preparation according to the invention for the treatment of anaemia patients comprises 500–10,000 U, in particular 2,000–4,000 U of an EPO preparation and 3–10 mg, preferably 5 mg iron ions, preferably of a Fe(III) complex in which the EPO preparation and the Fe(III) complex can be present in separate forms of administration or in a uniform form of administration.

The forms of administration according to the invention also enable the iron preparations to be administered 1 to 3 days before the EPO administration in order to already fill up the iron stores before the start of the EPO treatment.

The invention also concerns the use of 1,000–10,000 U of an EPO preparation and 5–20 mg iron ions of a physiologically compatible iron preparation to produce combination preparations for the treatment of haemodialysis patients.

In clinical chemistry the concentration of iron in blood and the iron binding capacity are determined to examine iron metabolism. Both tests should always be carried out since the relationship between the measured results is important. The normal serum iron level in men is usually between 75 and 150 mg/dl and between 60 and 140 mg/dl in women. The total iron binding capacity is between 250 and 450 mg/dl. The serum iron level varies during the day. It is decreased in iron deficiency and in anaemias caused by chronic diseases. It is increased in haemolysis and in syndromes with iron overloading (e.g. haemochromatosis or haemosiderosis). Patients undergoing an oral iron medication may have a normal iron serum level although they actually have an iron deficiency. The total iron binding capacity (=transferrin×2) is increased in iron deficiency whereas it is decreased in anaemias in the course of chronic diseases.

In addition the serum ferritin level is determined. Ferritin is an iron-storing glycoprotein of which tissue typical isoferritins exist that can be immunologically determined in the serum e.g. by a radioimmunoassay (RIA) and also by turbidimetric methods. The ferritin value is a measure of the iron storage in the tissue. In most laboratories the normal range is between 30 and 300 ng/ml and the geometric mean is 88 in males and 49 in females. The serum ferritin values are closely related to the total iron store of the body. Hence a decreased serum ferritin level is only found in iron deficiency. Increased levels are found in iron overloading. An increased serum level of ferritin is also found in liver damage or in association with some neoplasias where ferritins can also be bound to acute phase proteins. The serum transferrin receptor can also be determined by an enzyme-amplified immuno-absorption test (enzyme-linked immunosorbent assay=ELISA). In this method a monoclonal antibody to the soluble receptor is used. The reference range is between 0.5–3 mg/l. The level is increased when there is a slight deficiency in the iron stores. The concentration of specific erythrocyte ferritins can be determined in order to characterize the iron stores especially when the serum ferritin cannot be utilized in the case of tissue damage or in acute phase reactions.

In addition the erythrocyte ferritin level is also determined to examine iron metabolism. In heparinized blood erythrocytes are separated by centrifugation from the leucocytes and thrombocytes (which also contain ferritin). The erythrocytes are then lysed and the stored ferritin is determined immunologically. The erythrocyte ferritin reflects the status of the iron stores during the last three months (i.e. during the lifetime of an erythrocyte). The normal values are usually between 5 and 48 attogram (ag) per erythrocyte. Values <5 are found in iron deficiency anaemias and increased values (often >100) in the case of iron overloading (e.g. haemochromatosis). The determination of zinc protoporphyrin is of similar value.

Clinical Studies:

Patients are treated with a weekly dose of 5–30 mg of an iron(III) complex and a weekly dose of an EPO preparation of a total of 7,000–15,000 U. Both preparations are in each case administered on the same day. The iron status of the patients is measured by determining the diagnostic parameters transferrin, transferrin saturation, CRP, GOT/GPT and γ-GT. If the ferritin value is in the normal range of <500 µg/l then the patient is optimally controlled.

What is claimed is:

1. A method of treating disturbances in iron metabolism in a patient undergoing haemodialysis or treatment for anemia, which comprises administering to such patient:
   (a) an erythropoietin preparation that provides active erythropoietin in an amount of from about 250 U to less than about 2,000 U, and
   (b) an iron preparation that comprises a physiologically compatible iron salt or iron complex compound that provides from 1 mg to 30 mg of iron ions;
   the administration occurring during both the correction phase and the maintenance phase of the treatment without changing the amount of the erythropoietin preparation or the iron preparation being administered, wherein the weekly amount of the erythropoietin preparation provides from 7,000 U to 15,000 U of active erythropoietin and the weekly amount of the iron preparation provides from 5 mg to 30 mg of iron ions.

2. The method of claim 1, wherein the both the erythropoietin preparation and the iron preparation are administered from one to five times per week.

3. The method of claim 1, wherein the erythropoietin preparation provides from about 500 U to less than about 2,000 U of active erythropoietin.

4. The method of claim 1, wherein the erythropoietin preparation provides from about 1,000 U to less than about 2,000 U of active erythropoietin.

5. The method of claim 1, wherein the iron preparation provides between 5 mg and 20 mg of iron ions.

6. The method of claim 1, wherein the iron salt or the iron complex is selected from the group consisting of iron(II)sulfate, iron(II)fumarate, iron(III)citrate, iron(II)gluconate, iron(II)succinate, iron(II)chloride, iron(II)glycine-sulfate complex, iron(II)aspartate, sodium-iron(III)gluconate complex, iron(III)-hydroxide-polymaltose complex, and ferrisorbitol citrate complex.

7. The method of claim 1, wherein the iron preparation comprises an iron complex.

8. The method of claim 7, wherein the iron complex is a Fe(III) complex.

9. The method of claim 8, wherein the Fe(III) complex has a molecular weight of 30,000–100,000 D.

10. The method of claim 9, wherein the Fe(III) complex is a Fe(III)-saccharate.

11. The method of claim 9, wherein the Fe(III) complex is a Fe(III)gluconate.

12. The method of claim 11 wherein the Fe(III)gluconate is present in an amount of about 5 mg and the erythropoietin preparation provides about 1500 U of active erythropoietin, the administration of both the iron and the etythropoietin occurring from one to five times per week.

13. The method of claim 12 wherein the administration of both the iron and erythropoietin occurs five times per week.

* * * * *